US011195036B2

(12) United States Patent
Park et al.

(10) Patent No.: US 11,195,036 B2
(45) Date of Patent: Dec. 7, 2021

(54) METHOD AND APPARATUS FOR DETERMINING FOOTPRINT IDENTITY USING DIMENSION REDUCTION ALGORITHM

(71) Applicant: REPUBLIC OF KOREA (NATIONAL FORENSIC SERVICE DIRECTOR MINISTRY OF THE INTERIOR AND SAFETY), Wonju-si (KR)

(72) Inventors: Nam Kyu Park, Bucheon-si (KR); Jae Mo Goh, Wonju-si (KR); Jin Pyo Kim, Daejeon (KR); Young Il Seo, Wonju-si (KR); Eun Ah Joo, Yongin-si (KR); Je Hyun Lee, Wonju-si (KR); Sang Yoon Lee, Wonju-si (KR); Kyung Mi Kim, Namyangju-si (KR); Gang Won Byun, Gwangju-si (KR)

(73) Assignee: REPUBLIC OF KOREA (NATIONAL FORENSIC SERVICE DIRECTOR MINISTRY OF THE INTERIOR AND SAFETY), Wonju-si (KR)

( * ) Notice: Subject to any disclaimer, the term of this patent is extended or adjusted under 35 U.S.C. 154(b) by 0 days.

(21) Appl. No.: 17/038,363

(22) Filed: Sep. 30, 2020

(65) Prior Publication Data

US 2021/0350157 A1 Nov. 11, 2021

(30) Foreign Application Priority Data

May 7, 2020 (KR) .................. 10-2020-0054667

(51) Int. Cl.
*G06K 9/00* (2006.01)
*G06K 9/62* (2006.01)

(52) U.S. Cl.
CPC ..... *G06K 9/00885* (2013.01); *G06K 9/00201* (2013.01); *G06K 9/6215* (2013.01); *G06K 2009/00946* (2013.01)

(58) Field of Classification Search
None
See application file for complete search history.

(56) References Cited

FOREIGN PATENT DOCUMENTS

| KR | 10-2013-0142723 A | 12/2013 |
| KR | 10-2017-0053069 A | 5/2017 |
| KR | 10-1767380 B1 | 8/2017 |

OTHER PUBLICATIONS

Office Action issued for corresponding Korean Patent Application No. 10-2020-0054667 dated Sep. 27, 2021, along with a partial English translation.

*Primary Examiner* — Edward Park
(74) *Attorney, Agent, or Firm* — Hauptman Ham, LLP

(57) ABSTRACT

A method of determining footprint identity using a dimension reduction algorithm according to an embodiment includes: pre-processing to process three-dimensional (3D) image data about footprints of a first person and a second person and convert the 3D image data into one-dimensional (1D) data about the footprints of the first person and the second person; calculating a distribution of cross-correlation coefficients between two pieces of 1D data about footprints of the first person (SC: same footwear correlation) and a distribution of cross-correlation coefficients between the 1D data about the footprints of the first person and the second person (DC: difference footwear correlation); and calculating a likelihood ratio based on the SC and the DC to determine the degree of correspondence between the footprints of the first person and the second person.

8 Claims, 9 Drawing Sheets

(a)

(b)

(a)

(b)

METHOD AND APPARATUS FOR DETERMINING FOOTPRINT IDENTITY USING DIMENSION REDUCTION ALGORITHM

CROSS-REFERENCE TO RELATED APPLICATION

This application claims the benefit of Korean Patent Application No. 10-2020-0054667, filed on May 7, 2020, in the Korean Intellectual Property Office, the disclosure of which is incorporated herein in its entirety by reference.

BACKGROUND

1. Field

One or more embodiments relate to a method and an apparatus for determining footprint identity using a dimension reduction algorithm.

2. Description of the Related Art

At a crime scene, traces of suspect's action may be found. Footprints are traces of shoes a criminal left at the crime scene. Trace evidence, such as footprints, fingerprints, and tool marks, is closely related to a crime. Footprints, like fingerprints and tool marks in criminal cases, play an important role in estimating criminals and reconstructing the scene.

Factors that determine footprint identity include a unit pattern and size and shape of a pattern, which are cluster characteristics of footprints, the number and shapes of imprint marks and wear marks, which are individual characteristics of the footprints, and the like. It is possible to determine the footprint identity by evaluating results derived from experiments comparing footprints of a suspect and footprints remaining at the crime scene.

In this way, in evaluating the results of the experiments comparing footprints to determine the footprint identity, the necessity of logical and stochastic approaches is forensically required.

[Prior art document] Korean Patent No. 10-1767380 (registered on Aug. 7, 2017)

SUMMARY

One or more embodiments include a method and an apparatus for determining footprint identity using a dimension reduction algorithm, determining the degree of correspondence between two footprints by calculating a likelihood ratio by obtaining a cross-correlation coefficient between data about the footprints after converting two-dimensional (2D) data about the footprints into one-dimensional (1D) data and reducing the dimension of the data.

According to one or more embodiments, a method of determining footprint identity using a dimension reduction algorithm includes: performing pre-processing to process three-dimensional (3D) image data about footprints of a first person and a second person and convert the 3D image data into 1D data about the footprints of the first person and the second person; calculating a distribution of cross-correlation coefficients between two pieces of 1D data about footprints of the first person (SC: same footwear correlation) and a distribution of cross-correlation coefficients between the 1D data about the footprints of the first person and the second person (DC: difference footwear correlation); and calculating a likelihood ratio based on the SC and the DC to determine the degree of correspondence between the footprints of the first person and the second person.

According to an embodiment, the pre-processing may include: converting the 3D image data about the footprints of the first person and the second person into 2D image data to extract 2D data about the footprints of the first person and the second person; and converting the 2D data about the footprints of the first person and the second person into the 1D data about the footprints of the first person and the second person.

According to an embodiment, the 1D data about the footprints of the first person and the second person and the 2D data about the footprints of the first person and the second person may be 1D data about cluster characteristics of the footprints of the first person and the second person and 2D data about cluster characteristics of the footprints of the first person and the second person, respectively.

According to an embodiment, the likelihood ratio may be represented by the following equation.

Likelihood ratio=SC distribution/DC distribution

According to one or more embodiments, an apparatus for determining footprint identity using a dimension reduction algorithm includes: a data preprocessor configured to pre-process to process 3D image data about footprints of first person and second person and convert the 3D image data into 1D data about the footprints of the first person and the second person; a cross-correlation coefficient distribution calculator configured to calculate a distribution of cross-correlation coefficients between two pieces of 1D data about footprints of the first person (SC: same footwear correlation) and a distribution of cross-correlation coefficients between the 1D data about the footprints of the first person and the second person (DC: difference footwear correlation); and a determiner configured to calculate a likelihood ratio based on the SC and the DC to determine the degree of correspondence between the footprints of the first person and the second person.

According to an embodiment, the data preprocessor may include: a data extractor configured to convert the 3D image data about the footprints of the first person and the second person into 2D image data to extract 2D data about the footprints of the first person and the second person; and a data converter configured to convert the 2D data about the footprints of the first person and the second person into the 1D data about the footprints of the first person and the second person.

According to an embodiment, the 1D data about the footprints of the first person and the second person and the 2D data about the footprints of the first person and the second person may be 1D data about cluster characteristics of the footprints of the first person and the second person and 2D data about cluster characteristics of the footprints of the first person and the second person, respectively.

According to an embodiment, the likelihood ratio may be represented by the following equation.

Likelihood ratio=SC distribution/DC distribution

Additional aspects will be set forth in part in the description which follows and, in part, will be apparent from the description, or may be learned by practice of the presented embodiments.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
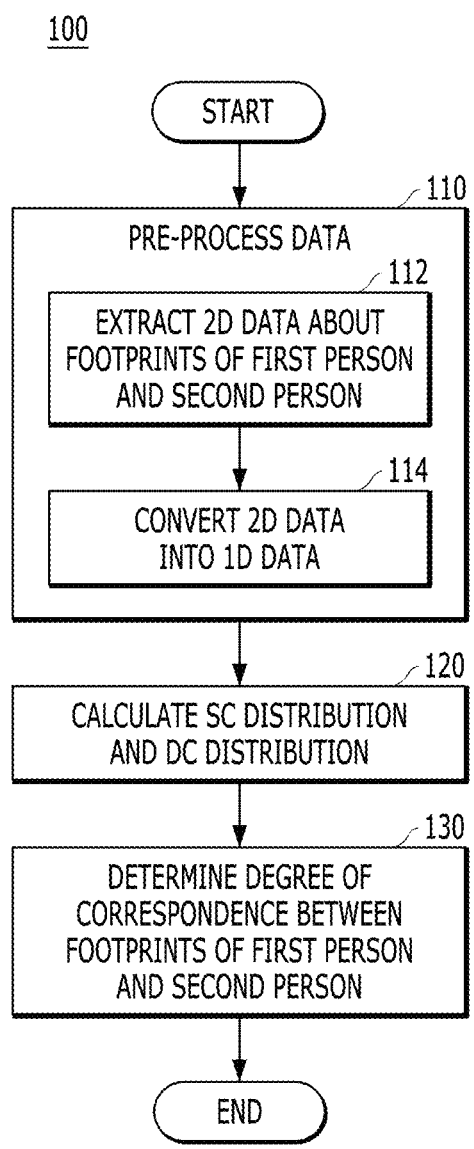
FIG. 1 is a flowchart illustrating a method of determining footprint identity using a dimension reduction algorithm, according to an embodiment.

Hereinafter, embodiments will be described in detail with reference to the accompanying drawings. The same reference numerals are used to denote the same elements, and repeated descriptions thereof will be omitted.

It will be understood that although the terms "first," "second," etc. may be used herein to describe various components, these components should not be limited by these terms.

An expression used in the singular encompasses the expression of the plural, unless it has a clearly different meaning in the context.

It will be further understood that the terms "comprises" and/or "comprising" used herein specify the presence of stated features or components, but do not preclude the presence or addition of one or more other features or components.

It will be understood that when a layer, region, or component is referred to as being "formed on" another layer, region, or component, it can be directly or indirectly formed on the other layer, region, or component. That is, for example, intervening layers, regions, or components may be present.

Sizes of elements in the drawings may be exaggerated for convenience of explanation. In other words, since sizes and thicknesses of components in the drawings are arbitrarily illustrated for convenience of description, the following embodiments are not limited thereto. When a certain embodiment may be implemented differently, a specific process order may be performed differently from the described order. For example, two consecutively described processes may be performed substantially at the same time or performed in an order opposite to the described order.

It will be understood that when a layer, region, or component is connected to another portion, the layer, region, or component may be directly connected to the portion or an intervening layer, region, or component may exist. For example, when a layer, region, or component is electrically connected to another portion, the layer, region, or component may be directly electrically connected to the portion or may be indirectly connected to the portion through another layer, region, or component.

Hereinafter, a method of determining footprint identity using a dimension reduction algorithm according to an embodiment will be described with reference to FIGS. 1 to 8.

Figure 2:
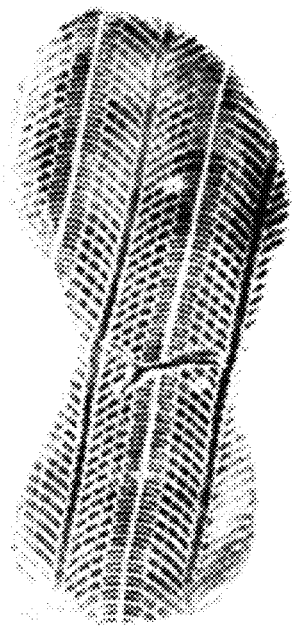
FIG. 2 is a view of two-dimensional (2D) images about footprints of a first person and a second person according to an embodiment.
Figure 2:
Figure 3:
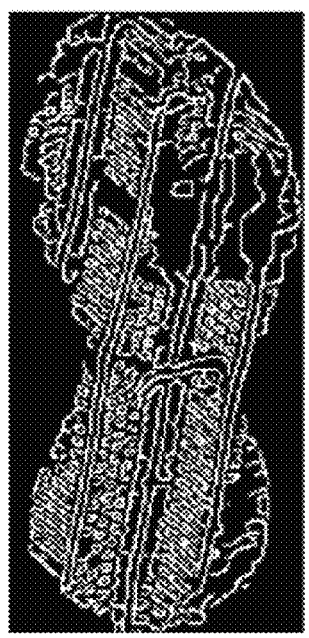
FIG. 3 is a view of images processed to extract cluster characteristics of footprints from the images of FIG. 2.
Figure 3:
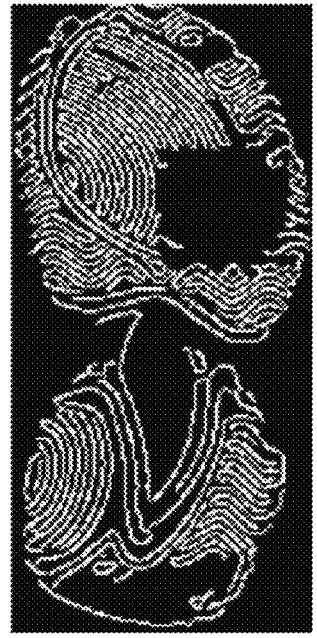

FIG. 1 is a flowchart illustrating a method of determining footprint identity using a dimension reduction algorithm, according to an embodiment. FIG. 2 is a view of two-dimensional (2D) images about footprints of a first person and a second person according to an embodiment. FIG. 3 is a view of images processed to extract cluster characteristics of footprints from the images of FIG. 2.

Referring FIG. 1, operation 110 may perform pre-processing to process 3D image data about footprints of a first person and a second person and convert the 3D image data into 1D data about the footprints of the first person and the second person.

Referring to FIG. 1, operation 110 is specifically as follows. The pre-processing (operation 110) may include operation 112 of converting the 3D image data about the footprints of the first person and the second person into 2D image data to extract 2D data about the footprints of the first person and the second person, and operation 114 of converting the 2D data about the footprints of the first person and the second person into the 1D data about the footprints of the first person and the second person.

Operation 112 may convert the 3D image data about the footprints of the first person and the second person into 2D image data to extract 2D data about the footprints of the first person and the second person.

A footprint is a trace of shoes found at a crime scene. The footprint may be obtained as an image or a photograph of a surface or a space containing the footprint. However, this is an example, and the disclosure is not limited thereto, and it is only necessary that it is an image or a photograph including a footprint regardless of an acquisition method. In this way, the footprint may be obtained as 3D image data. For example, a gray filter may be applied to 3D image data about a footprint, and may be expressed as 2D image data about the footprint as shown in FIG. 2. FIGS. 2 (*a*) and (*b*) show two different 2D images of the footprints of the first person and the second person. As described above, it is possible to obtain 2D image data about footprints, including images of the footprints of the first person and the second person at various angles. For example, 2D image data about a footprint provided by the Crime Scene Footwear Impression Database may be obtained.

The footprint of the first person found at the crime scene may be shot at different angles at different times. At this time, a plurality of 2D images about the footprint of the first person may be displayed in various ways on different coordinate systems. The images displayed on different coordinate systems may be registered and processed to be displayed on one coordinate system. In addition, 2D images about the footprint of the second person found in the crime scene may also be registered and processed to be displayed on one coordinate system.

For example, 2D image data about a footprint provided by the Crime Scene Footwear Impression Database may be read using an imread function built into MATLAB. In this way, 2D image data about a footprint taken at various angles may be read. At this time, 2D images about the footprint, taken at various angles using an imregister function, may be registered. Thereafter, an optimizer and a metric to register an image may be generated by setting a multimodal option using an imregconfig function. A minimum registration radius may be set by setting an IntitialRadius value to 0.00009 and an Epsilon value to 1.5e-4. Also, a size of a radius to be registered may be gradually increased by setting a GrowthFactor value to 1.01. Also, an image registration point may be found through 300 registration iterations by setting a MaximumIterations value to 300.

At this time, the registered 2D images about the footprint may be subjected to any one or more of image rotation, black-and-white processing, contour extraction processing, sharpen, skew processing, engraved-embossed conversion, and left-right symmetric processing to facilitate extracting cluster characteristics of the footprint. For example, as shown in FIG. 3, an edge function of MATLAB may be used to identify an edge of an object in a 2D image about a footprint through edge detection. At this time, the edge is a curve displayed along a path in which the contrast on an image changes rapidly. In this way, a unit pattern of a footprint and size and shape of a pattern, which are cluster characteristics of the footprint may be extracted by detecting a discontinuous edge of the contrast on a 2D image about a footprint. The unit pattern of the footprint means the most basic shape that constitutes a certain area of the footprint. 2D data about cluster characteristics of a footprint may be extracted based on 2D image data about the footprint.

In this way, the 3D image data about the footprints of the first person and the second person may be converted into 2D image data, and the converted 2D image data may be registered and processed by a process such as edge detection, thereby extracting the 2D data about the footprints of the first person and the second person. Here, the extracted data may be 2D data about the cluster characteristics of the footprints of the first person and the second person. In this case, the 2D data is data in a 2D array format in which array elements of data are represented by rows and columns.

In operation 114, the 2D data about the footprints of the first person and the second person may be converted into 1D data about the footprints of the first person and the second person. In this case, the 1D data is data in a 1D array format in which array elements of data are represented by one line. Here, the 1D data about the footprints of the first person and the second person and the 2D data about the footprints of the first person and the second person may be 1D data about cluster characteristics of the footprints of the first and second people, and 2D data about cluster characteristics of the footprints of the first person and the second person, respectively.

When the 2D data about the footprints of the first person and the second person are converted into 1D data, a cross-correlation coefficient between the data may be calculated. For example, by changing the size and shape of a data array using MATLAB or a Python's reshape function, the 2D data about the footprints of the first person and the second person may be converted into 1D data. By performing data pre-processing to reduce the dimension of data in this way, it may be possible to calculate a cross-correlation coefficient between data to be described later below.

In operation 120, it is possible to calculate a distribution of cross-correlation coefficients between two pieces of 1D data about footprints of the first person (SC: same footwear correlation) and a distribution of cross-correlation coefficients between the 1D data about the footprints of the first person and the second person (DC: difference footwear correlation).

A cross-correlation coefficient is an index that may confirm statistical similarity between two or more different pieces of data. For example, a MATLAB's xcorr function may be used to obtain the cross-correlation coefficient. At this time, the cross-correlation coefficient may have a value between 0 and 1 by setting a 'coeff' option in the MATLAB's xcorr function. The cross-correlation coefficient may have a value between 0 and 1 depending on the degree of statistical similarity. A value of the cross-correlation coefficient when two pieces of data are not completely equal is 0, and a value of the cross-correlation coefficient when the two pieces of data are completely identical is 1.

Cross-correlation coefficients between two pieces of 1D data about footprints of the first person (SC: same footwear correlation) may be obtained. The largest value of the SC obtained in this way is stored. A distribution of these stored values may be determined through a Quantile-Quantile (Q-Q) plot.

In the same way, cross-correlation coefficients between 1D data about the footprints of the first person and the second person (DC: difference footwear correlation) may be obtained. The largest value of the DC obtained in this way is stored. A distribution of these stored values may be determined through a Q-Q plot.

Figure 4:
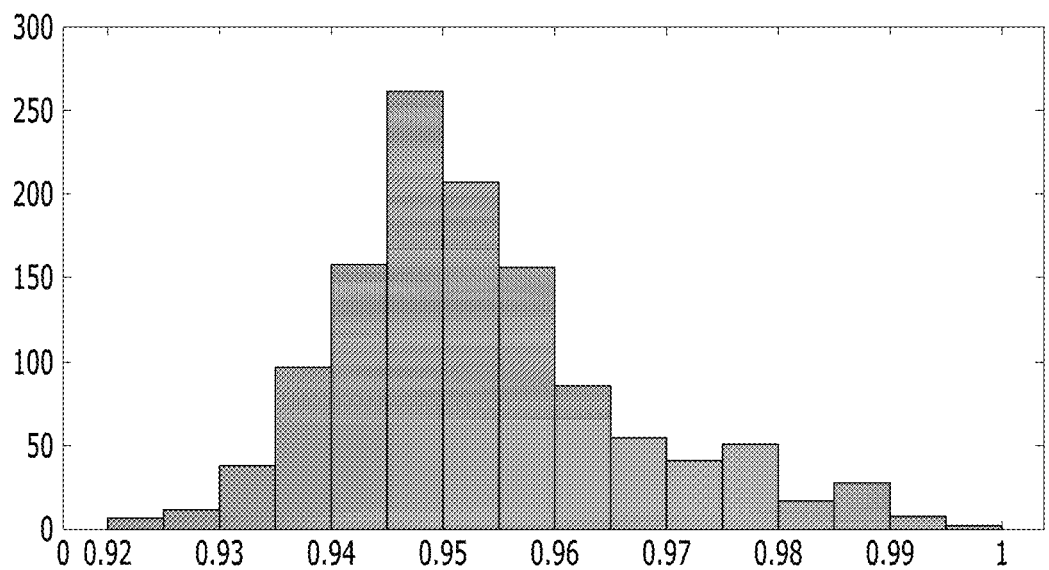
FIG. 4 is a graph illustrating the relationship between frequency and cross-correlation coefficients (SC) between two pieces of one-dimensional (1D) data about footprints of a first person.

FIG. 4 is a graph illustrating the relationship between frequency and SC. Here, an X-axis represents a value of the SC, and a Y-axis represents the frequency. Referring to FIG. 4, cross-correlation coefficients (SC) between two pieces of 1D data about footprints of a first person, the same footprints, are distributed based on 0.95, and the maximum value is 1 and the minimum value is 0.9202.

Figure 5:
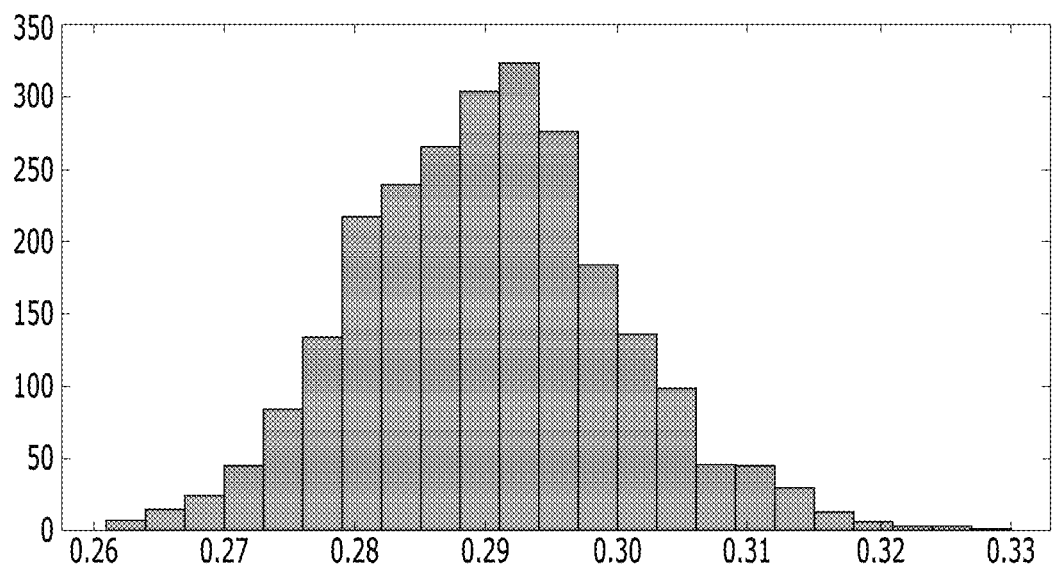
FIG. 5 is a graph illustrating the relationship between frequency and cross-correlation coefficients (DC) between 1D data about footprints of a first person and a second person.

FIG. 5 is a graph illustrating the relationship between frequency and DC. Here, an X-axis represents a value of the DC, and a Y-axis represents the frequency. Referring to FIG. 5, cross-correlation coefficients (DC) between 1D data about footprints of a first person and a second person, different footprints, are distributed based on 0.29, and the maximum value is 0.3277 and the minimum value is 0.2611.

In short, referring to FIGS. 4 and 5, it can be seen that the SC, which are cross-correlation coefficients between data about the same footprint, have a larger value than the DC, which are cross-correlation coefficients between data about different footprints.

The SC and DC obtained as described above may be selected and stored, respectively, and a distribution of the stored values may be determined by drawing a Q-Q plot. The Q-Q plot is a method that compares probability distributions of two distributions with each other and visually determines the similarity between the two distributions. The Q-Q plot makes it possible to visually check whether data follow a specific distribution. An X-axis of the Q-Q plot may represent a theoretical quantile according to a specific distribution, and a Y-axis may represent a quantile of an input sample (the X-axis and Y-axis may be changed). At this time, the quantile is a cut point that divides the range of a probability distribution into successive intervals with the same probability.

Figure 6A:
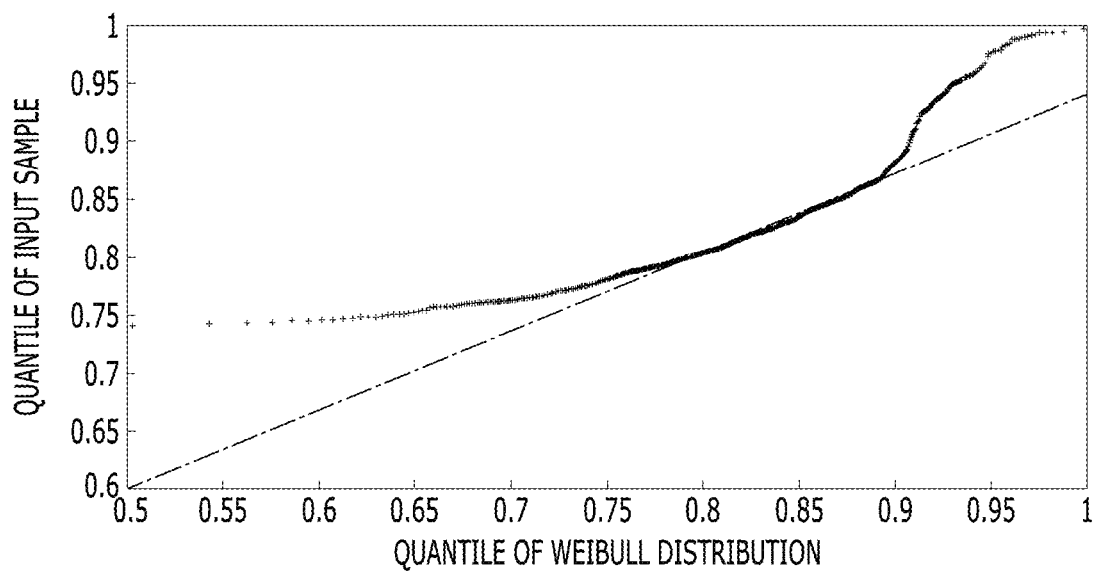
FIG. 6A is a Q-Q plot of a Weibull distribution of SC.
Figure 6B:
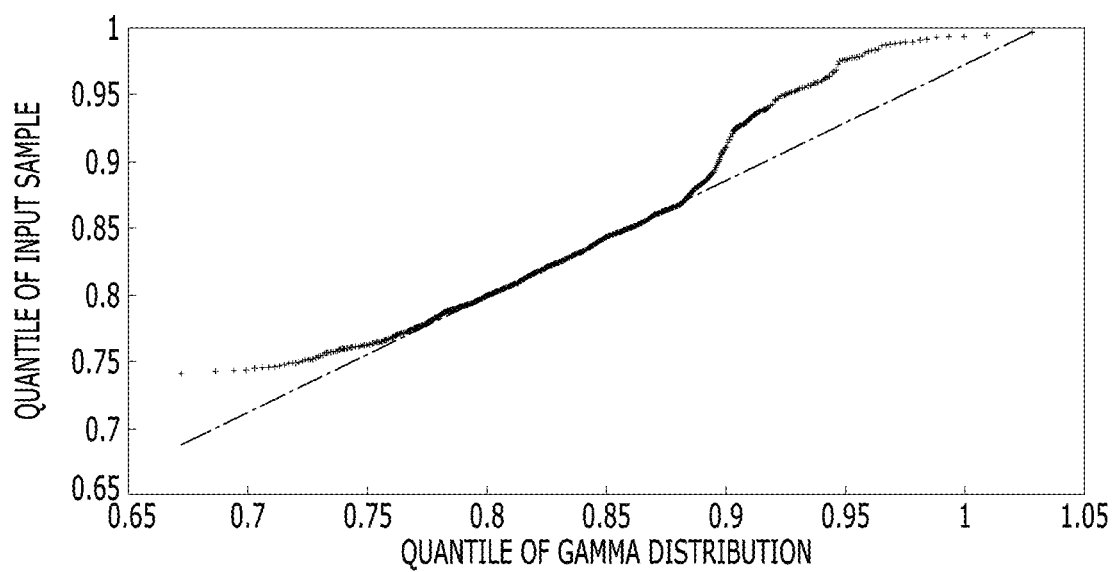
FIG. 6B is a Q-Q plot of a gamma distribution of SC.
Figure 6C:
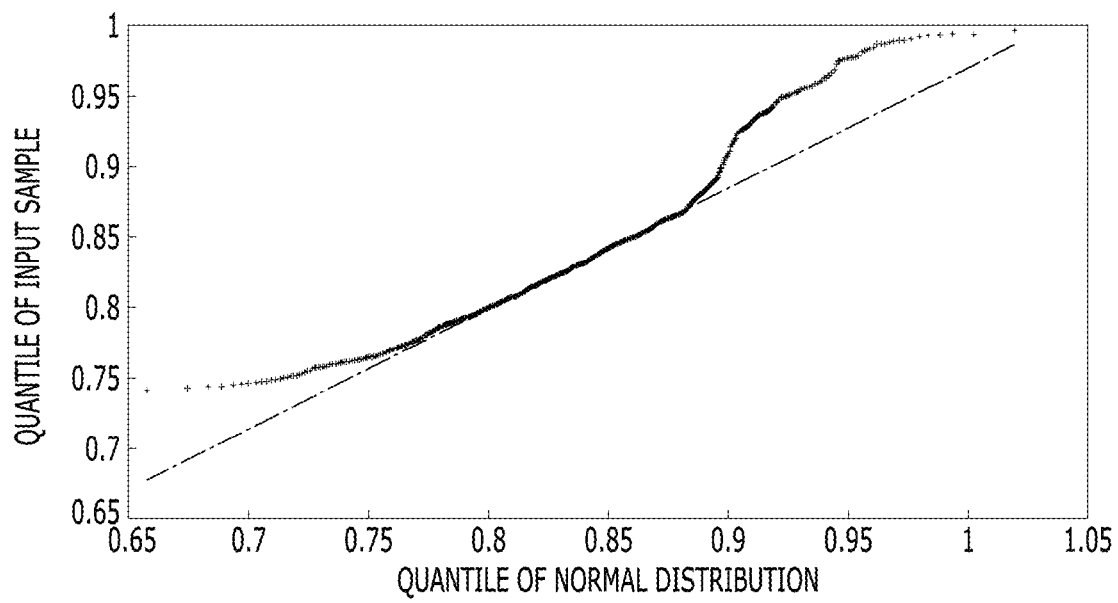
FIG. 6C is a Q-Q plot of a normal distribution of SC.
Figure 6D:
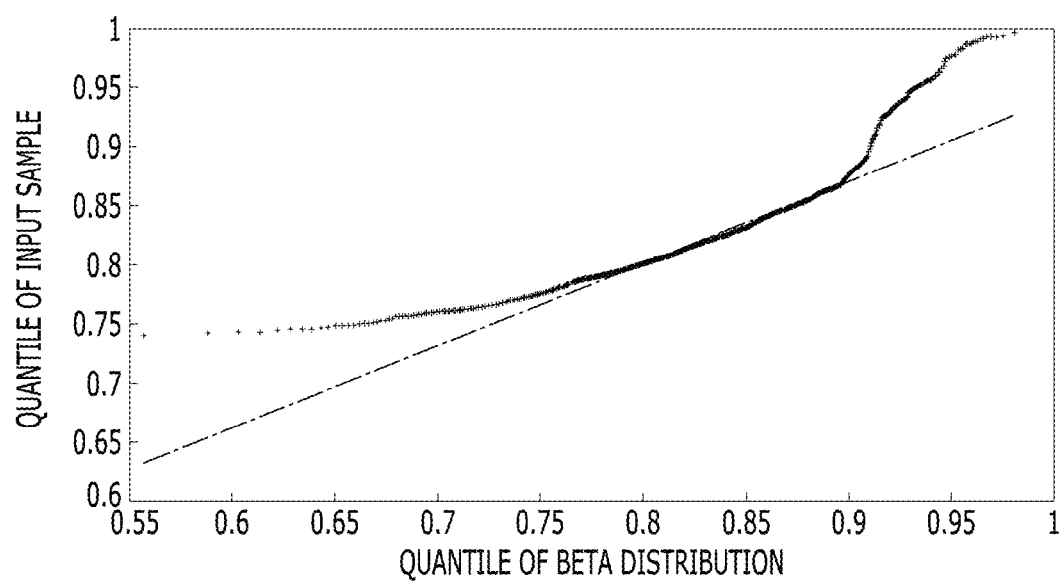
FIG. 6D is a Q-Q plot of a beta distribution of SC.

FIGS. 6A to 6D are Q-Q plots showing distributions of SC. FIG. 6A is a Q-Q plot of a Weibull distribution of SC, and FIG. 6B is a Q-Q plot of a gamma distribution of SC. FIG. 6C is a Q-Q plot of a normal distribution of SC, and FIG. 6D is a Q-Q plot of a beta distribution of SC.

Figure 7A:
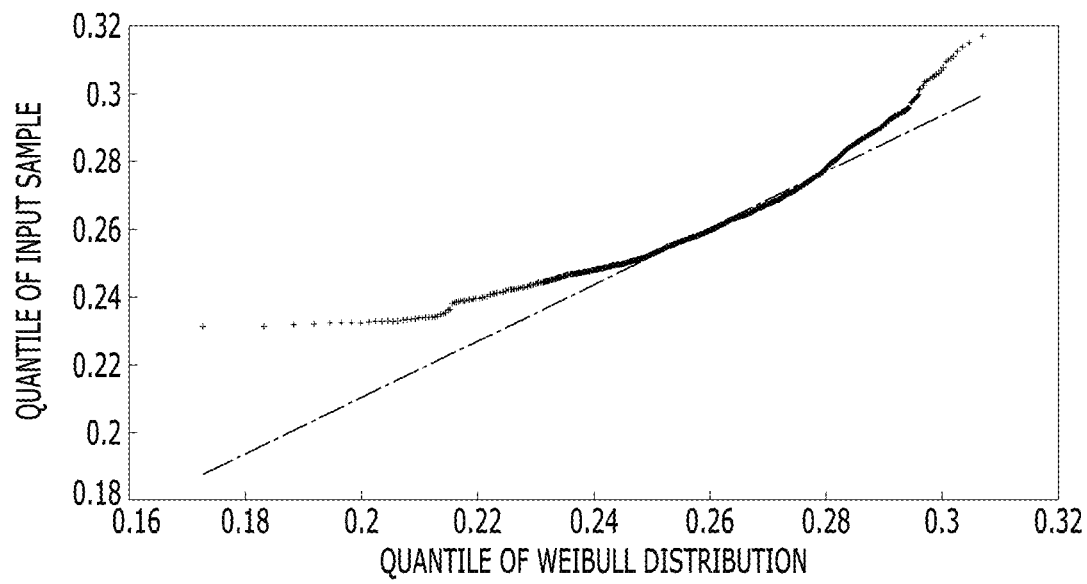
FIG. 7A is a Q-Q plot of a Weibull distribution of DC.
Figure 7B:
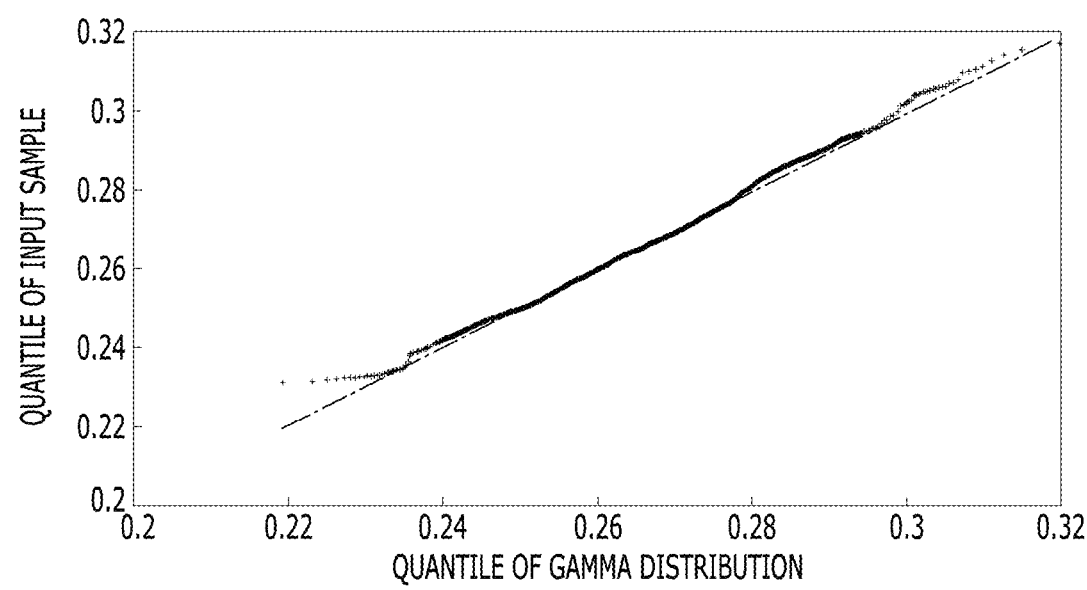
FIG. 7B is a Q-Q plot of a gamma distribution of DC.
Figure 7C:
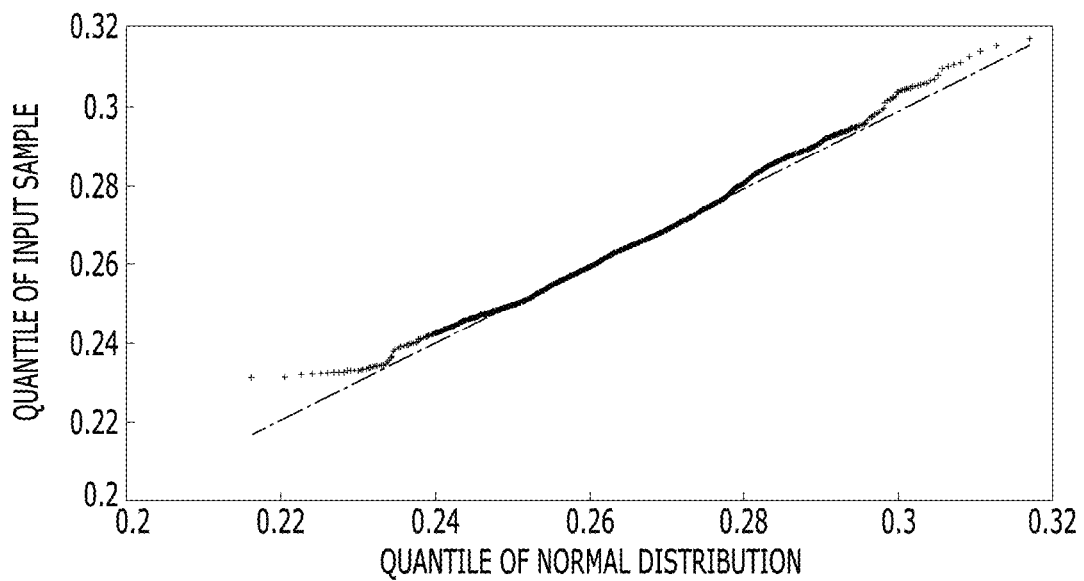
FIG. 7C is a Q-Q plot of a normal distribution of DC.
Figure 7D:
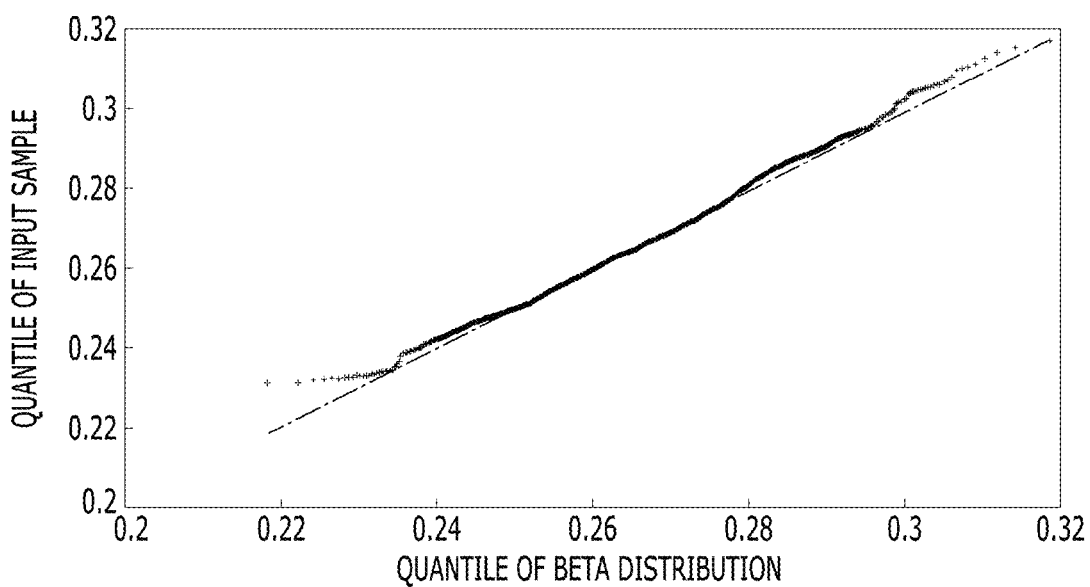
FIG. 7D is a Q-Q plot of a beta distribution of DC.

FIGS. 7A to 7D are Q-Q plots showing distributions of DC. FIG. 7A is a Q-Q plot of a Weibull distribution of DC, and FIG. 7B is a Q-Q plot of a gamma distribution of DC. FIG. 7C is a Q-Q plot of a normal distribution of DC, and FIG. 7D is a Q-Q plot of a beta distribution of DC.

As a result of plotting the Q-Q plot as described above, referring to FIGS. 6A to 6D, it can be confirmed that the SC follows a normal distribution. In addition, referring to FIGS. 7A to 7D, it can be confirmed that the DC follows a beta distribution.

In operation 130, a likelihood ratio based on the SC and the DC may be calculated to determine the degree of correspondence between footprints of a first person and a second person.

The likelihood ratio may be calculated and determined by a statistical method to confirm footprint identity. Using the likelihood ratio, a prosecution hypothesis and a defense hypothesis may be compared to verify whether there is a significant difference between the two hypotheses. Here, when the prosecution hypothesis about footprint identity is $H_P$ and the defense hypothesis is $H_D$, the two hypotheses set are as follows.

$H_P$: Shoes found at a crime scene are suspect's shoes.
$H_D$: The shoes found at the crime scene are someone's shoes, not the suspect's.

At this time, the likelihood ratio is obtained by dividing a prosecution probability by a defense probability. The likelihood ratio may be expressed by dividing a probability density function of the $H_P$ by a probability density function of the $H_D$. When the likelihood ratio is greater than 1, it can be interpreted that the prosecution hypothesis may be supported X times more than the defense hypothesis, and when the likelihood ratio is less than 1, it can be interpreted that the defense hypothesis may be supported X times more than the prosecution hypothesis.

The likelihood ratio according to an embodiment may be expressed based on the SC and the DC. In an embodiment, the prosecution probability is a probability when the footprint of first person and a footprint of a suspect found at the crime scene are the same, and may be expressed in correspondence with an SC distribution, which is a distribution of cross-correlation coefficients between two pieces of 1D data about footprints of the first person. The defense probability is a probability when the footprint of the first person and the footprint of the suspect found at the crime scene are not the same, and may be expressed in correspondence with a DC distribution which is a distribution of cross-correlation coefficients between 1D data about the footprint of the first person and the footprint of the second person different from the first person.

Accordingly, the likelihood ratio according to an embodiment may be represented by a value obtained by dividing the SC distribution by the DC distribution.

That is, Likelihood ratio=SC distribution/DC distribution

At this time, when the SC distribution follows the normal distribution and the DC distribution follows the beta distribution, as in FIGS. 6A to 6D and FIGS. 7A to 7D, the likelihood ratio may be calculated by dividing an SC normal distribution by a DC beta distribution.

Figure 8:
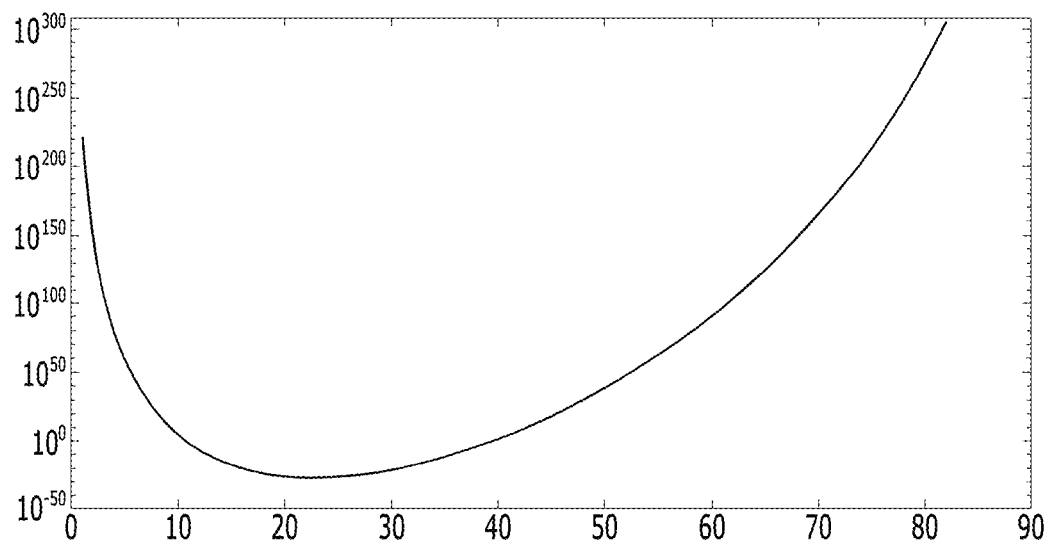
FIG. 8 is a graph illustrating a likelihood ratio calculated according to an embodiment.

FIG. 8 is a graph exemplarily showing a likelihood ratio calculated according to an embodiment. An X-axis represents values of SC and DC, and a Y-axis represents the likelihood ratio. As shown in FIG. 8, the likelihood ratio according to the values of the SC and the DC may be expressed on a graph, and by calculating a quantitative value of the likelihood ratio and determining the degree of correspondence between two footprints, footprint identity may be statistically represented.

Figure 9:
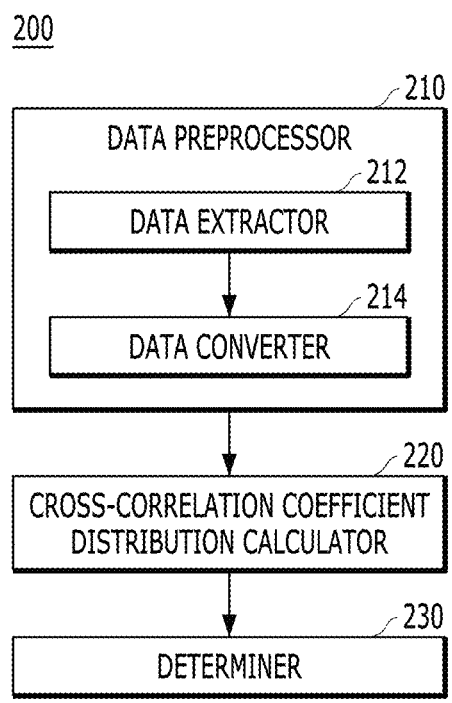
FIG. 9 is a block diagram of an apparatus for determining footprint identity using a dimension reduction algorithm, according to an embodiment.

FIG. 9 is a block diagram of an apparatus for determining footprint identity using a dimension reduction algorithm, according to an embodiment.

Referring to FIG. 9, an apparatus 200 for determining footprint identity using a dimension reduction algorithm according to an embodiment may include a data preprocessor 210, a cross-correlation coefficient distribution calculator 220, and a determiner 230.

The data preprocessor 210 may perform pre-processing to process 3D image data about footprints of a first person and a second person and convert the data into 1D data about the footprints of the first person and the second person. Referring to FIG. 9, the data preprocessor 210 may include a data extractor 212 and a data converter 214.

The data extractor 212 may convert the 3D image data about the footprints of the first person and the second person into 2D image data, and may extract 2D data about the footprints of the first person and the second person. In this case, the 2D data about the footprints of the first person and the second person may be 2D data about cluster characteristics of the footprints of the first person and the second person. Here, the cluster characteristics of the footprints mean a unit pattern and size and shape of a pattern. In addition, the 2D data about the cluster characteristics of the footprints of the first person and the second person is data in the form of a 2D array.

The data converter 214 may convert the 2D data about the footprints of the first person and the second person into the 1D data about the footprints of the first person and the second person. Here, the 2D data about the footprints of the first person and the second person may be 2D data about cluster characteristics of the footprints of the first person and the second person. Also, the 1D data about the footprints of the first person and the second person may be 1D data about the cluster characteristics of the footprints of the first person and the second person. At this time, the 1D data is data in the form of a 1D array. In this way, the data converter 214 converts 2D data into 1D data to enable calculation of cross-correlation coefficients between data.

The cross-correlation coefficient distribution calculator 220 may calculate a distribution of cross-correlation coefficients between two pieces of 1D data about footprints of the first person (SC) and a distribution of cross-correlation coefficients between the 1D data about the footprints of the first person and the second person (DC). After obtaining the 1D data about the footprints of the first person and the second person through the data preprocessor 210, the cross-correlation coefficients between the two pieces of 1D data about footprints of the first person (SC) and the cross-correlation coefficients between the 1D data about the footprints of the first person and the second person (DC) may be obtained. The largest value of each of the SC and the DC obtained in this way may be selected and stored, respectively, and a distribution of the stored values may be determined by drawing a Q-Q plot.

The determiner 230 may calculate a likelihood ratio based on the SC and the DC to determine the degree of correspondence between the footprints of the first person and the second person.

At this time, the likelihood ratio may be expressed by the following equation.

Likelihood ratio=SC distribution/DC distribution

As such, the likelihood ratio calculated based on the SC and the DC may be expressed on a graph as shown in FIG. 8. By quantitatively determining the degree of correspondence between two footprints according to the calculated likelihood ratio, footprint identity may be statistically represented.

The apparatus 200 for determining footprint identity using a dimension reduction algorithm according to an embodiment shows only components associated with the present embodiment in order to prevent features of the present embodiment is blurred. Accordingly, it is to be understood by one of ordinary skill in the art that other general-purpose components may be further included in addition to the components shown in FIG. 9.

Figure 10:
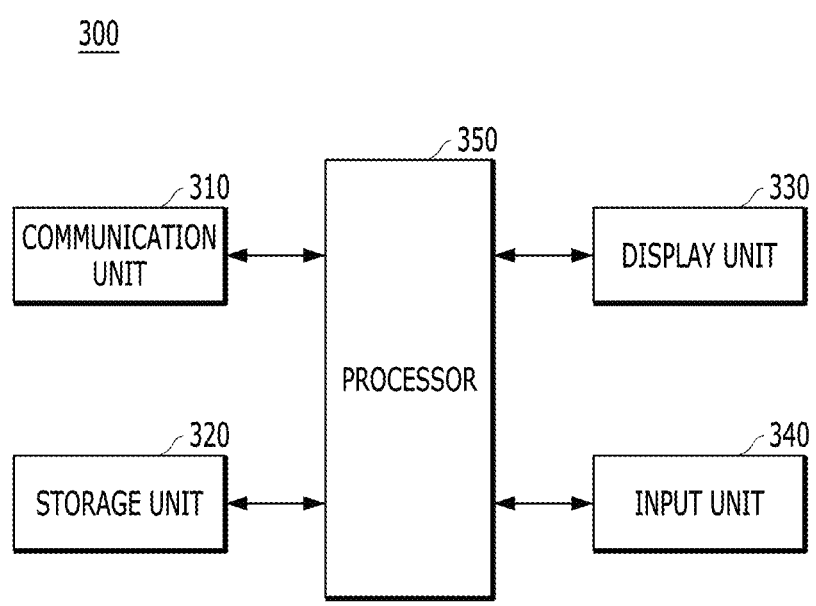
FIG. 10 is a block diagram of an exemplary computer device for implementing an embodiment.

FIG. 10 is a block diagram of an exemplary computer device for implementing an embodiment. In addition, terms such as " . . . unit" refer to units that perform at least one function or operation, and the units may be implemented as hardware or software or as a combination of hardware and software.

Referring to FIG. 10, a computer device 300 may include a communication unit 310, a storage unit 320, a display unit 330, an input unit 340, and a processor 350.

The communication unit 310 provides an interface for communicating with other systems or devices. For example, the communication unit 310 may include an interface device used to connect with a network interface card, Ethernet, a token ring, or another type of physical coupling material that enables communication via an external network. For example, the communication unit 310 may perform signal processing for accessing a wireless network. The computer device 300 may be connected to a number of clients and servers through conventional network infrastructure, such as the Internet.

The storage unit 320 may store data such as a basic program, an application program, and setting information for the operation of the computer device 300. The storage unit 320 may be configured of a volatile memory, a non-volatile memory, or a combination of the volatile memory and the nonvolatile memory. In addition, the storage unit 320 may provide data stored at the request of the processor 350.

The display unit 330 performs functions for outputting information in the form of numbers, letters, images, graphics, and the like. To this end, the display unit 330 may include at least one hardware module for output. For example, the hardware module may include at least one of a liquid crystal display (LCD), a light emitting diode (LED), a light emitting polymer display (LPD), an organic LED (OLED), an active matrix OLED (AMOLED), and a flexible LED (FLED). That is, the display unit 330 may display a screen corresponding to data received from the processor 350. The display unit 330 may be referred to as an output unit, a display unit, or another term having an equivalent technical meaning.

The input unit 340 detects an input from the outside (e.g., a user) and provides data corresponding to the input to the processor 350. To this end, the input unit 340 may include at least one hardware module for detecting the input. For example, the hardware module may include at least one of a sensor, a keyboard, a keypad, a touch pad, and a touch panel. According to an embodiment, when the input unit 340 is implemented as a touch panel, the input unit 340 may be combined with the display unit 330 to provide a touch screen. In this case, the input unit 340 may provide data about a user's touch input to the processor 350.

The processor 350 controls the overall operations of the computer device 300. For example, the processor 350 transmits and receives a signal through the communication unit 310. In addition, the processor 350 writes and reads data in the storage unit 320 and executes instructions stored in the storage 320. In addition, the processor 350 may display various screens through the display unit 330. Furthermore, the processor 350 may process data input through the input unit 340 and control an operation state of the input unit 340 as necessary. The processor 350 may include one or multiple processors.

According to an embodiment, quantitative criteria for footprint identity may be provided by calculating a likelihood ratio based on cross-correlation coefficients between data and probabilistically evaluating the degree of correspondence between two footprints after converting 2D data about cluster characteristics of footprints into 1D data and reducing the dimension of data.

Hereinabove, all components according to the embodiments are described to be combined as one or are described to operate by being combined with each other, but the disclosure is not limited thereto. In other words, at least two of the components may selectively combine to operate within the scopes of the disclosure.

Also, each of the components may be realized as independent hardware, or some or all of the components may be selectively combined to be realized as a computer program having a program module in which some or all functions are performed in one or more hardware. Codes, and code segments for configuring the computer program may be easily construed by one of ordinary skill in the art to which embodiments belong.

Such a computer program may be stored in a computer readable medium and read and executed by a computer, thereby implementing the embodiment. Examples of the computer readable medium of the computer program may be a magnetic recording medium, an optical recording medium, or the like.

Unless otherwise defined, all terms (including technical and scientific terms) used herein have the same meaning as commonly understood by one of ordinary skill in the art to which embodiments belong. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The description herein is for the purpose of describing the disclosure and numerous modifications and adaptations will be readily apparent to one of ordinary skill in the art without departing from the spirit and scope of the disclosure.

In this regard, the present embodiments may have different forms and should not be construed as being limited to the descriptions set forth herein. While the disclosure has been particularly shown and described with reference to embodiments thereof, it will be understood that various changes in form and details may be made therein without departing from the spirit and scope of the following claims.

As described above, a method 100 and the apparatus 200 for determining footprint identity using a dimension reduction algorithm according to the embodiments may reduce the dimension of data by converting 2D data about cluster characteristics of footprints into 1D data, and then may calculate a likelihood ratio of two footprints by obtaining a cross-correlation coefficient, thereby quantitatively determining the degree of correspondence between the two footprints. In addition, embodiments may effectively contribute to the resolution of crime cases by enabling both forensic science and law practitioners to have a logical approach to evaluating footprint identity based on probability.

What is claimed is:

1. A method of determining footprint identity using a dimension reduction algorithm, the method comprising:

performing pre-processing to process three-dimensional (3D) image data about footprints of a first person and a second person and convert the 3D image data into one-dimensional (1D) data about the footprints of the first person and the second person;

calculating a distribution of cross-correlation coefficients between two pieces of 1D data about footprints of the first person (SC: same footwear correlation) and a distribution of cross-correlation coefficients between the 1D data about the footprints of the first person and the second person (DC: difference footwear correlation); and calculating a likelihood ratio based on the SC and the DC to determine the degree of correspondence between the footprints of the first person and the second person.

2. The method of claim 1, wherein the performing of the pre-processing comprises:

converting the 3D image data about the footprints of the first person and the second person into two-dimensional (2D) image data to extract 2D data about the footprints of the first person and the second person; and converting the 2D data about the footprints of the first person and the second person into 1D data about the footprints of the first person and the second person.

3. The method of claim 2, wherein the 1D data about the footprints of the first person and the second person and the 2D data about the footprints of the first person and the second person are 1D data about cluster characteristics of the footprints of the first person and the second person and 2D data about cluster characteristics of the footprints of the first person and the second person, respectively.

4. The method of claim 1, wherein the likelihood ratio is expressed by the following equation:

Likelihood ratio=SC distribution/DC distribution.

5. An apparatus for determining footprint identity using a dimension reduction algorithm, the apparatus comprising:

a data preprocessor configured to perform pre-processing to process three-dimensional (3D) image data about footprints of a first person and a second person and convert the 3D image data into 1D data about the footprints of the first person and the second person;

a cross-correlation coefficient distribution calculator configured to calculate a distribution of cross-correlation coefficients between two pieces of one-dimensional (1D) data about footprints of the first person (SC: same footwear correlation) and a distribution of cross-correlation coefficients between the 1D data about the footprints of the first person and the second person (DC: difference footwear correlation); and a determiner configured to calculate a likelihood ratio based on the SC and the DC to determine the degree of correspondence between the footprints of the first person and the second person.

6. The apparatus of claim 5, wherein the data preprocessor comprises:

a data extractor configured to convert the 3D image data about the footprints of the first person and the second person into two-dimensional (2D) image data to extract 2D data about the footprints of the first person and the second person; and a data converter configured to convert the 2D data about the footprints of the first person and the second person into the 1D data about the footprints of the first person and the second person.

7. The apparatus of claim 6, wherein the 1D data about the footprints of the first person and the second person and the 2D data about the footprints of the first person and the second person are 1D data about cluster characteristics of the footprints of the first person and the second person and 2D data about cluster characteristics of the footprints of the first person and the second person, respectively.

8. The apparatus of claim 5, wherein the likelihood ratio is expressed by the following equation:

Likelihood ratio=SC distribution/DC distribution.

* * * * *